(12) United States Patent
Hwang et al.

(10) Patent No.: US 9,198,880 B2
(45) Date of Patent: Dec. 1, 2015

(54) **USE OF PANDURATIN DERIVATIVES OR AN EXTRACT OF *BOESENBERGIA PANDURATA* FOR PROMOTING MUSCLE MASS GROWTH, FIGHTING FATIGUE, AND ENHANCING EXERCISE PERFORMANCE CAPABILITY**

(71) Applicants: Biocare Co., Ltd., Seoul (KR); Newtree Co., Ltd., Seongnam, Gyeonggi-do (KR)

(72) Inventors: Jae-Kwan Hwang, Gyeonggi-do (KR); Do Un Kim, Gyeonggi-do (KR)

(73) Assignees: Biocare Co., Ltd., Seoul (KR); Newtree Co., Ltd., Sungnam, Gyeongi-do (KR)

( * ) Notice: Subject to any disclaimer, the term of this patent is extended or adjusted under 35 U.S.C. 154(b) by 0 days.

(21) Appl. No.: 13/682,216

(22) Filed: Nov. 20, 2012

(65) Prior Publication Data

US 2013/0344182 A1    Dec. 26, 2013

(30) Foreign Application Priority Data

May 20, 2010    (KR) .................... 10-2010-0047369

(51) Int. Cl.
*A01N 65/00*    (2009.01)
*A61K 31/12*    (2006.01)
*A61K 36/00*    (2006.01)
*A61K 36/906*    (2006.01)
*A23L 1/30*    (2006.01)

(52) U.S. Cl.
CPC .............. *A61K 31/12* (2013.01); *A23L 1/3002* (2013.01); *A61K 36/00* (2013.01); *A61K 36/906* (2013.01)

(58) Field of Classification Search
CPC ...................................................... A61K 36/00
USPC .......................................................... 424/725
See application file for complete search history.

(56) References Cited

PUBLICATIONS (J. Appl. Physiol. 2003, 95, p. 1717-1727).*

* cited by examiner

*Primary Examiner* — Michael Meller
(74) *Attorney, Agent, or Firm* — Mintz Levin Cohn Ferris Glovsky and Popeo, P.C.; Kongsik Kim; Richard B. Emmons

(57) ABSTRACT

The present invention relates to the novel use of panduratin derivatives or an extract of *Boesenbergia pandurata* for enhancing muscle mass growth, fighting fatigue and enhancing exercise performance. A panduratin derivative or a salt thereof or an extract of *Boesenbergia pandurata* of the present invention may be used without side effect and has the effect of increasing the expression of PPAR-δ in muscles to increase muscle mass, promoting recovery from fatigue and increase mobility, thereby improving exercise performance.

1 Claim, 3 Drawing Sheets

USE OF PANDURATIN DERIVATIVES OR AN EXTRACT OF *BOESENBERGIA PANDURATA* FOR PROMOTING MUSCLE MASS GROWTH, FIGHTING FATIGUE, AND ENHANCING EXERCISE PERFORMANCE CAPABILITY

TECHNICAL FIELD

This application claims priority from and the benefit of Korean Patent Application No. 10-2010-0047369, filed on May 20, 2010, which is hereby incorporated by reference for all purposes as if fully set forth herein.

The present invention relates to the novel use of panduratin derivatives or an extract of *Boesenbergia pandurata* for enhancing muscle mass growth, fighting fatigue and enhancing exercise performance, and more particularly to a composition for promoting an increase in muscles, anti-fatigue composition and a composition for enhancing muscle mass growth and recovery from fatigue to improve exercise performance, the composition comprising a panduratin derivative or a salt thereof or an extract of *Boesenbergia pandurata* as an active ingredient, and to a method for enhancing muscle mass growth, of treating or preventing fatigue syndrome and enhancing exercise performance, the method comprising a panduratin derivative or a salt thereof or a extract of *Boesenbergia pandurata* to a subject in need thereof.

BACKGROUND ART

Generally, when muscles are not regularly trained, the muscular function will be impaired due to aging, and decreases in muscle mass and neuromuscular junctions (motor unit) will occur, and thus the body will feel fatigue easily and will become languid, thus reducing the vital power of the body and rapidly reducing the quality of life (J. Appl. Physiol. 2003, 95, p 1717-1727). For this reason, it is recommended that exercise such as resistance training be regularly performed (Korean Patent Laid-Open Publication No. 10-2009-0089815) together with suitable dietary therapy. As described above, regular exercise is required to improve the quality of life, and not only athletes but also general people require more energy and endurance in daily life. However, modern people who are pressed with a busy daily life mostly tend to depend on dietary supplements. Thus, studies on supplements, functional foods, food compositions and the like for improving physical exercise performance ability have been conducted for a long period of time. In fact, it is known that the intake of compounds such as steroids and caffeine increases exercise capability. However, such drugs can be accompanied with fatal side effects, and thus the use thereof is extremely limited.

Skeletal muscle fibers are generally classified into type 1 (oxidative/slow) and type 2 (glycolytic/fast) fibers, and there are significant differences in contraction, metabolism and susceptibility to fatigue between muscle fiber types. Type 1 fiber is rich in mitochondria and uses oxidative metabolism to produce energy, and thus can steadily supply ATP for a long period of time to resist fatigue. Accordingly, muscle consumption does not occur in skeletal muscles rich in type 1 fiber (Muscle Nerve 2005, 31, p 339-348). Type 2 fiber lacks mitochondria and oxidative enzymes and depends on glycolytic metabolism as a major energy resource, and thus is easily fatigued.

PPAR-δ (peroxisome proliferator activated receptor δ) is a major transcription regulator which is abundantly present mainly in skeletal muscles, particularly type 1 fiber (10 folds of PPAR-α, and 50 folds of PPAR-γ) and activates enzymes associated with the beta oxidation of long-chain fatty acids to burn fat in adipose cells (Cell 2003, 113, p 159-170). Also, it is a first transcription factor that stimulates the formation of type 1 fiber. It is known that PPAR-δ regulates mitochondrial biosynthesis when being activated and is involved in complex pathways which improve exercise capability and increase resistance to obesity (PLOS Biology 2004, 2, p 1532-1539). Thus, type 1 fiber made adaptively by exercise is known to have high resistance to fatigue. Thus, it was reported that the artificial overexpression of PPAR-δ shows the same effects as exercise. When PPAR-δ was artificially overexpressed in the muscles of mice, mitochondrial biosynthesis increased and the expression of fatty acid beta-oxidase and type 1 muscle fiber also increased, and thus continuous running time and distance increased by 67% and 92%, respectively, compared to those for general mice (PLOS Biology 2004, 2, p 1532-1539). Therefore, when PPAR-δ is activated, the type of muscle fiber can be changed, resulting in an increase in exercise performance ability.

DISCLOSURE

Technical Problem

Accordingly, the present inventors have conducted studies on the investigation of natural materials that increase intramuscular PPAR-δ activity and have excellent safety, and as a result, have found that an extract of *Boesenbergia pandurata*, a plant belonging to the Zingiberaceae family, and a panduratin derivative isolated therefrom, increase the expression of intramuscular PPAR-δ protein and promote muscle enhancement and recovery from fatigue to improve exercise performance ability, thereby completing the present invention.

It is an object of the present invention to provide a composition for enhancing exercise performance comprising a panduratin derivative or a salt thereof as an active ingredient.

Another object of the present invention is to provide a composition for enhancing exercise performance comprising an extract of *Boesenbergia pandurata* as an active ingredient.

Still another object of the present invention is to provide a composition for enhancing muscle mass growth comprising a panduratin derivative or a salt thereof as an active ingredient.

Still another object of the present invention is to provide a composition for enhancing muscle mass growth comprising an extract of *Boesenbergia pandurata* as an active ingredient.

Still another object of the present invention is to provide an anti-fatigue composition comprising a panduratin derivative or a salt thereof as an active ingredient.

Still another object of the present invention is to provide an anti-fatigue composition comprising an extract of *Boesenbergia pandurata* as an active ingredient.

Still another object of the present invention is to provide a method for enhancing exercise performance comprising administering an effective amount of a panduratin derivative or a salt thereof to a subject in need thereof.

Still another object of the present invention is to provide the use of a panduratin derivative or a salt thereof for preparing an agent for enhancing exercise performance.

Still another object of the present invention is to provide a method for enhancing exercise performance comprising administering an effective amount of an extract of *Boesenbergia pandurata* to a subject in need thereof.

Still another object of the present invention is to provide the use of an extract of *Boesenbergia pandurata* for preparation of an agent for enhancing exercise performance.

Still another object of the present invention is to provide a method for enhancing muscle mass growth comprising administering an effective amount of a panduratin derivative or a salt thereof to a subject in need thereof.

Still another object of the present invention is to provide the use of a panduratin derivative or a salt thereof for preparation of an agent for enhancing muscle mass growth.

Still another object of the present invention is to provide a method for enhancing muscle mass growth comprising administering an effective amount of an extract of *Boesenbergia pandurata* to a subject in need thereof.

Still another object of the present invention is to provide the use of an extract of *Boesenbergia pandurata* for preparation of an agent for enhancing muscle mass growth.

Still another object of the present invention is to provide a method of treating or preventing fatigue syndrome comprising administering an effective amount of a panduratin derivative or a salt thereof to a subject in need thereof.

Still another object of the present invention is to provide the use of a panduratin derivative or salt thereof for preparing of an anti-fatigue agent.

Still another object of the present invention is to provide a method of treating or preventing fatigue syndrome comprising administering an effective amount of an extract of *Boesenbergia pandurata* to a subject in need thereof.

Still another object of the present invention is to provide the use of an extract of *Boesenbergia pandurata* for preparing of for preparing of an anti-fatigue agent.

Technical Solution

To achieve the above object, the present invention provides a composition for enhancing exercise performance comprising a panduratin derivative or a salt thereof as an active ingredient.

To achieve another object, the present invention provides a composition for enhancing exercise performance comprising an extract of *Boesenbergia pandurata* as an active ingredient.

To achieve still another object, the present invention provides a composition for enhancing muscle mass growth comprising a panduratin derivative or a salt thereof as an active ingredient.

To achieve still another object, the present invention provides a composition for enhancing muscle mass growth comprising an extract of *Boesenbergia pandurata* as an active ingredient.

To achieve still another object, the present invention provides an anti-fatigue composition comprising a panduratin derivative or a salt thereof as an active ingredient.

To achieve still another object, the present invention provides an anti-fatigue composition comprising an extract of *Boesenbergia pandurata* as an active ingredient.

To achieve still another object, the present invention provides a method for enhancing exercise performance comprising administering an effective amount of a panduratin derivative or a salt thereof to a subject in need thereof.

To achieve still another object, the present invention provides the use of a panduratin derivative or a salt thereof for preparing an agent for enhancing exercise performance.

To achieve still another object, the present invention provides a method for enhancing exercise performance comprising administering an effective amount of an extract of *Boesenbergia pandurata* to a subject in need thereof.

To achieve still another object, the present invention provides the use of an extract of *Boesenbergia pandurata* for preparing an agent for enhancing exercise performance.

To achieve still another object, the present invention provides a method for enhancing muscle mass growth comprising administering an effective amount of a panduratin derivative or a salt thereof to a subject in need thereof.

To achieve still another object, the present invention provides the use of a panduratin derivative or a salt thereof for preparing an agent for enhancing muscle mass growth.

To achieve still another object, the present invention provides a method for enhancing muscle mass growth comprising administering an effective amount of an extract of *Boesenbergia pandurata* to a subject in need thereof.

To achieve still another object, the present invention provides the use of an extract of *Boesenbergia pandurata* for preparing an agent for enhancing muscle mass growth.

To achieve still another object, the present invention provides a method of treating or preventing fatigue syndrome comprising administering an effective amount of a panduratin derivative or a salt thereof to a subject in need thereof.

To achieve still another object, the present invention provides the use of a panduratin derivative or salt thereof for preparing of an anti-fatigue agent.

To achieve still another object, the present invention provides a method of treating or preventing fatigue syndrome comprising administering an effective amount of an extract of *Boesenbergia pandurata* to a subject in need thereof.

To achieve still another object, the present invention provides the use of an extract of *Boesenbergia pandurata* for preparation of an anti-fatigue agent.

Hereafter, the present invention is described in detail.

The composition of the present invention comprises, as an active ingredient, a panduratin derivative or a salt thereof which increases the expression of PPAR-δ in muscle cells to increase muscle mass and promotes recovery from fatigue, thereby enhancing exercise performance.

The panduratin derivatives include panduratin A represented by the following formula 1, 4-hydroxypaduratin A represented by the following formula 2, and isopanduratin A represented by the following formula 3. Panduratin A is (2,6-dihydroxy-4-methoxyphenyl)[3-methyl-2-(3-methylbut-2-enyl)-5-phenylcyclohex-3-enyl]methanone and has a molecular formula of $C_{26}H_{30}O_4$. 4-hydroxypanduratin A is (2,4,6-trihydroxyphenyl[3-methyl-2-(3-methylbut-2-enyl)-6-phenylcyclohex-3-enyl]methanone and has a molecular formula of $C_{25}H_{28}O_4$. Isopanduratin A is (2-methoxy-4,6-dihydroxyphenyl)-[3-methyl-2-(3-methylbut-2-enyl)-6-phenylcyclohex-3-enyl]methanone and has a molecular formula of $C_{26}H_{30}O_4$.

The panduratin derivatives are commercially available materials or can be prepared by known synthesis methods. Alternatively, the panduratin derivatives can be obtained by isolation and purification from an extract of *Boesenbergia pandurata* or oil obtained by pressing a *Boesenbergia pandurata* plant.

[Formula 1]

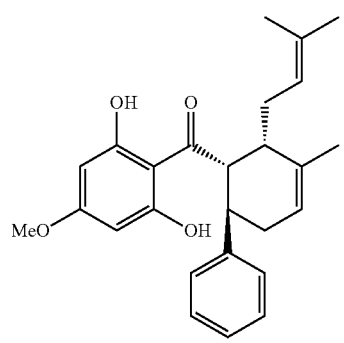

-continued

[Formula 2]

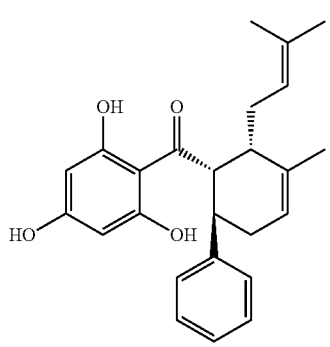

[Formula 3]

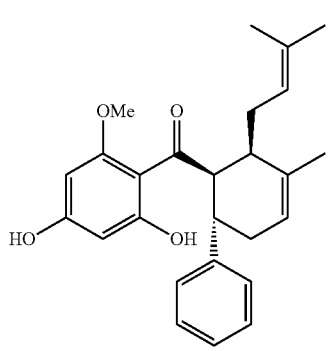

A panduratin derivative comprised in a composition of the present invention may be prepared by isolating and purifying rhizome of dry *Boesenbergia pandurata* using distilled water acceptable for food processing, ethanol and subcritical water or supercritical carbon dioxide, or from oil obtained by pressing *Boesenbergia pandurata*. To obtain a panduratin derivative comprised in a composition of the present invention or extract comprising thereof, as an extraction solvent, methanol, propanol, isopropanol, butanol, acetone, ether, benzene, chloroform, ethylacetate, methylenechloride, hexane, cyclohexane, petroliumether may be used alone or in combination as well as above-mentioned solvent.

For the isolation and purification of the panduratin derivative from the extract of *Boesenbergia pandurata*, column chromatography or high-performance liquid chromatography (HPLC) using silica gel, activated alumina or various other synthetic resins may be used alone or in combination, although not limited thereto.

The composition of the present invention is characterized in that it has the effect of improving exercise performance ability. "Exercise performance ability" is closely connected with the performance of athletes and improvement in records and can be improved by improvement in cardiorespiratory function, promotion of energy metabolism, recovery from fatigue and an increase in muscle strength. In other words, exercise performance ability can be improved by quick recovery from fatigue, which is accumulated upon a long period of training, and increasing exercise endurance. The composition of the present invention functions to increase the expression of PPAR-δ rich in type 1 fiber among skeletal muscle fibers. As described above, PPAR-δ is a factor that promotes the transcription of type 1 fiber. In muscles rich in type 1 fiber, PPAR-δ uses fat as an energy source, and thus lactic acid is not produced so that fatigue is not accumulated in muscles, thereby enhancing exercise performance.

The present invention also relates to a composition comprising an extract of *Boesenbergia pandurata* as an active ingredient. *Boesenbergia pandurata*, a plant belonging to the Zingiberaceae family, is also called *Kaempferia pandurata*. The extract of *Boesenbergia pandurata* contains components comprising pinocembrin chalcone, cardamonin, pinocembrin, pinostribin, 4-hydroxypaduratin A, panduratin A and isopanduratin A. The above components were reported to have anticancer effects (Trakoontivakorn, G. et al., J. Arig. Food Chem., 49, 30463050, 2001; Yun, J. M. et al., Carcinogenesis, 27(7), 14541464, 2006), anti-inflammatory effects (Yun, J. M. et al., Planta Medica, 69, 11021108, 2003), anti-skin aging effects (Shim, J. S. et al., Planta Medica, 74, 239244, 2008) or antibacterial effects (Hwang, J. K. et al, Int. J. Antimicrob. Agents, 23, 377381, 2004; Park, K. M. et al., Food Sci. Biotechnol., 14(2), 286-289, 2005). However, before the present invention, it was not reported that the above components have the effect of improving exercise performance ability by promoting muscle enhancement and recovery from fatigue.

In Examples of the present invention, panduratin A was extracted and isolated from *Boesenbergia pandurata* (see Examples 1 and 2).

In other Examples of the present invention, each of the isolated panduratin A and the *Boesenbergia pandurata* extract was administered to mice having high-fat-diet-induced mice, and as a result, it could be seen that the expression level of PPAR-δ in muscle cells, muscle mass, and mobility were increased (see Examples 3 to 5).

The panduratin derivative of the present invention may be used as it is or in the form of a pharmaceutically acceptable salt. As used herein, the phrase "pharmaceutically acceptable" means that the components present in the composition are physiologically acceptable and usually do not invoke allergic or similar reactions when administered to humans. Specifically, the salt may be an acid addition salt formed from a pharmaceutically acceptable free acid. The free acid may be an organic or inorganic acid. The organic acid includes but is not limited to citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid and aspartic acid. And, the inorganic acid includes but is not limited to hydrochloric acid, bromic acid, sulfuric acid and phosphoric acid.

The composition of the present invention is characterized in that it has the effect of promoting an increase in muscles. "Increase in muscles" means increasing muscular performance among the components of the body, and muscle mass can be increased by physical exercise and improvement in endurance, and by administering to the body a material having the effect of increasing muscles. Particularly, the composition of the present invention has the effect of promoting an increase in type 1 skeletal muscle fiber, but is not limited thereto.

The composition of the present invention is characterized in that it has an anti-fatigue effect. "Fatigue" is divided into mental fatigue and physical fatigue. As used herein, the term "fatigue" refers to physical fatigue which is accumulated in muscles after exercise performance, and physical fatigue is induced by intracellular glycogen accumulation, lactic acid dehydrogenase activity and citric acid synthase activity. The composition of the present invention has the effect of reducing the accumulation of fatigue in muscles by increasing the expression of PPAR-δ that promotes the transcription of type 1 skeletal muscle fiber capable of synthesizing a sufficient amount of ATP by oxidative metabolism.

A pharmaceutical composition of the present invention may be prepared in the form of a pharmaceutical composition or a food composition and it may comprise pharmaceutically effective amount of the panduratin derivative or the extract of *Boesenbergia pandurata* alone or together with one or more pharmaceutically acceptable carrier additionally. A pharmaceutical composition of the present invention may comprise 0.01 to 99.99 weight % of the panduratin derivative or the *Boesenbergia pandurata* extract and the rest may be a pharmaceutically acceptable carrier.

The pharmaceutically effective amount of the panduratin derivative or the *Boesenbergia pandurata* extract of the present invention may be 0.001 to 300 mg/day/kg body weight and preferably 0.01 to 200 mg/day/kg body weight/day. However, the pharmaceutically effective amount suitably determined by considering various factors, such as disease, severity thereof, age of patient, body weight, health condition, sex, diet administration route and administration time.

As used herein, "pharmaceutically acceptable" means non-toxic composition which is physiologically acceptable and, when administered to human beings, generally does not cause allergic reactions, such as gastrointestinal disorder and dizziness, or similar reactions thereto as well as not inhibiting reaction of an active ingredient. The carrier comprises all kinds of solvents, dispersing media, oil-in-water or water-in-oil emulsions, water soluble compositions, liposomes, microbeads and microsomes.

The pharmaceutical composition of the present invention may be formulated with a proper carrier according to administration routes. The administration routes of the pharmaceutical composition of the present invention comprise, but not limited thereto, oral or parenteral routes. The parenteral routes comprise, for example, subcutaneous, intranasal, peritorial, intramuscular, intracutaneous, or intravenous administration.

In case of the formulation for oral administration, the composition of the present invention may be formulated with a proper carrier for oral administration into powders, granules, tablets, pills, and sugar-coated tablets, capsules, liquids, gels, syrups, slurries, and emulsions by using the method known in the art.

For examples of appropriate carriers, it may comprise sugars comprising lactose, dextrose, sucrose, sorbitol, mannitol, xylitol, erythritol and maltitol, starches comprising corn starch, wheat starch, rice starch and potato starch, celluloses comprising cellulose, methyl cellulose, sodium carboxymethylcellulose and hydroxypropylmethylcellulose, and fillers comprising gelatin and polyvinylpyrrolidone. And, if desired, it may comprise cross-linked polyvinylpyrrolidone, agar, alginic acid or sodium alginate as a solutionizer. Further, the inventive pharmaceutical composition may comprise anti-coaglutinating agent, lubricant, wetting agents, flavors, emulsifying agents and antiseptics.

Also, in case of parenteral administration, a pharmaceutical composition of the present invention may be formulated with a proper carrier for parenteral administration into injections, transdermal preparations, and nasal inhalers by using the method known in the art. The injection must be sterilized and protected from microorganisms such as bacteria and fungi. Proper carriers for injection may be, but not limited thereto, water, ethanol, polyol (e.g. glycerol, propylene glycol and liquid polyethylene glycol) or mixture thereof and/or solvent or dispersing media comprising plant oil. More preferably, proper carriers may be Hank's solution, Ringer's solution, PBS (Phosphate buffered saline) containing triethanol amine, or a isotonic solution such as distilled water for injection, 10% ethanol, 40% ethanol, 40% propylene glycol and 5% dextrose.

To protect the injection from contamination of microorganisms, it may further comprise various antibiotics or antifungal reagent such as paraben, chlorobutanol, phenol, sorbic acid, thimerosal. In addition, in most cases, the injection may further comprise an isotonic reagent such as sugars or sodium chloride.

In case of transdermal preparations, it comprises ointments, creams, lotions, gels, topical solutions, paster, liniments and aerosols. The "transdermal preparations" means administering a pharmaceutical composition partially to skin and delivering effective amount of an active ingredient through the skin. The formulation of the above-mentioned is well described in Remington's Pharmaceutical Science, 15th Edition, 1975.

In case of nasal inhalers, a compound of the present invention may be delivered with a form of aerosol spray from pressure pack or spray by using proper propellants such as dichlorofluoromethane, trichlorofluoromethane, dichlorotetrafluoroethane, carbon dioxide or other proper gas. In case of pressure aerosols, dose may be determined by providing valve which delivers the measured amount of a compound. For example, a gelatin capsule and cartridge for inhaler or insufflator may be formulated to contain compound, and proper powder compound such as lactose or starch.

Other pharmaceutically acceptable carriers are well described in Remington's Pharmaceutical Sciences, 19th Edition, Mack Publishing Company, Easton, Pa., 1995.

Also, a pharmaceutical composition of the present invention may further comprise one or more buffers (e.g. saline or PBS), carbohydrates (e.g. glucose, mannose, sucrose or dextran), antioxidant, bacteriostat, chelating agent (e.g. EDTA or glutathione), adjuvant (e.g. aluminium hydroxide), suspension agent, thickening agent and/or preservative.

The panduratin derivative or the *Boesenbergia pandurata* extract of the present invention may be provided in the form of a food composition for enhancing muscle mass growth and providing anti-fatigue effects. The food composition of the present invention encompasses all food types comprising functional food, nutritional supplements, health food, food additives and animal feed, for humans or animals comprising livestock. The food composition may be prepared into various forms according to methods known in the related art.

For example, the health food may be prepared into the form of tea, juice or drink for drinking. Alternatively, the panduratin derivative or the *Boesenbergia pandurata* extract of the present invention may be formulated into granule, capsule or powder. In addition, the panduratin derivative or the extract of *Boesenbergia pandurata* may be formulated by mixing with other known active ingredients effective in enhancing muscle mass growth and providing anti-fatigue effects.

Also, the functional food may be prepared by adding the panduratin derivative or the extract of *Boesenbergia pandurata* of the present invention to beverages (including alcoholic beverages), fruits and processed foods thereof (e.g.: canned fruits, bottled fruits, jam, marmalade and the like), fishes, meats and processed foods thereof (e.g.: ham, sausages, corn beef), bread and noodles (e.g.: Japanese noodles, buckwheat noodles, ramen, spaghetti, macaroni and the like), juices, drinks, cookies, Korean taffy, dairy products (e.g.: butter, cheese and the like), eatable plant oils, margarine, plant proteins, retort foods, frozen foods, various seasonings (e.g.: soybean paste, soy sauce, sauce and the like).

Also, to use the panduratin derivative or the extract of *Boesenbergia pandurata* of the present invention for food additives, it may be formulated into powder or concentrated solution.

Preferable amount of the panduratin derivative or the extract of *Boesenbergia pandurata* in a food composition of the present invention may be 0.01 to 100 weight % and the rest may be an acceptable carrier for food compositions.

Meanwhile, the present invention provides a method for enhancing exercise performance comprising administering an effective amount of a panduratin derivative or a salt thereof to a subject in need thereof. Further, the present invention provides the use of a panduratin derivative or a salt thereof for preparing an agent for enhancing exercise performance.

Meanwhile, the present invention provides a method for enhancing exercise performance comprising administering an effective amount of an extract of *Boesenbergia pandurata* to a subject in need thereof. Further, the present invention provides the use of a an extract of *Boesenbergia pandurata* for preparing an agent for enhancing exercise performance.

Meanwhile, the present invention provides a method for enhancing muscle mass growth comprising administering an effective amount of a panduratin derivative or a salt thereof to a subject in need thereof. Further, the present invention provides the use of a panduratin derivative or a salt thereof for preparation of an agent for enhancing muscle mass growth.

Meanwhile, the present invention provides a method for enhancing muscle mass growth comprising administering an effective amount of an extract of *Boesenbergia pandurata* to a subject in need thereof. Further, the present invention provides the use of an extract of *Boesenbergia pandurata* for preparation of an agent for enhancing muscle mass growth.

Meanwhile, the present invention provides a method of treating or preventing fatigue syndrome comprising administering an effective amount of a panduratin derivative or a salt thereof to a subject in need thereof. Further, the present invention provides the use of a panduratin derivative or salt thereof for preparing of an anti-fatigue agent.

Meanwhile, the present invention provides a method of treating or preventing fatigue syndrome comprising administering an effective amount of an extract of *Boesenbergia pandurata* to a subject in need thereof. Further, the present invention provides the use of an extract of *Boesenbergia pandurata* for preparing of an anti-fatigue agent.

As used herein, the "effective amount" refers to the amount effective in enhancing exercise performance or enhancing muscle mass growth or providing anti-fatigue effects, and the "subject" refers to mammals, particularly, animals comprising human. The subject may be patient in need of enhancing exercise performance or enhancing muscle mass growth or providing anti-fatigue effects.

Advantageous Effects

As seen foregoing, the present invention provides a composition (or a method, use) for enhancing muscle mass growth, an anti-fatigue composition and a composition for enhancing exercise performance comprising a panduratin derivative or a salt thereof or an extract of *Boesenbergia pandurata*. A panduratin derivative or a salt thereof or an extract of *Boesenbergia pandurata* of the present invention may be used without side effect and has the effect of increasing the expression of PPAR-δ in muscles to increase muscle mass, promoting recovery from fatigue and increase mobility, thereby improving exercise performance.

MODE FOR INVENTION

Figure 1:
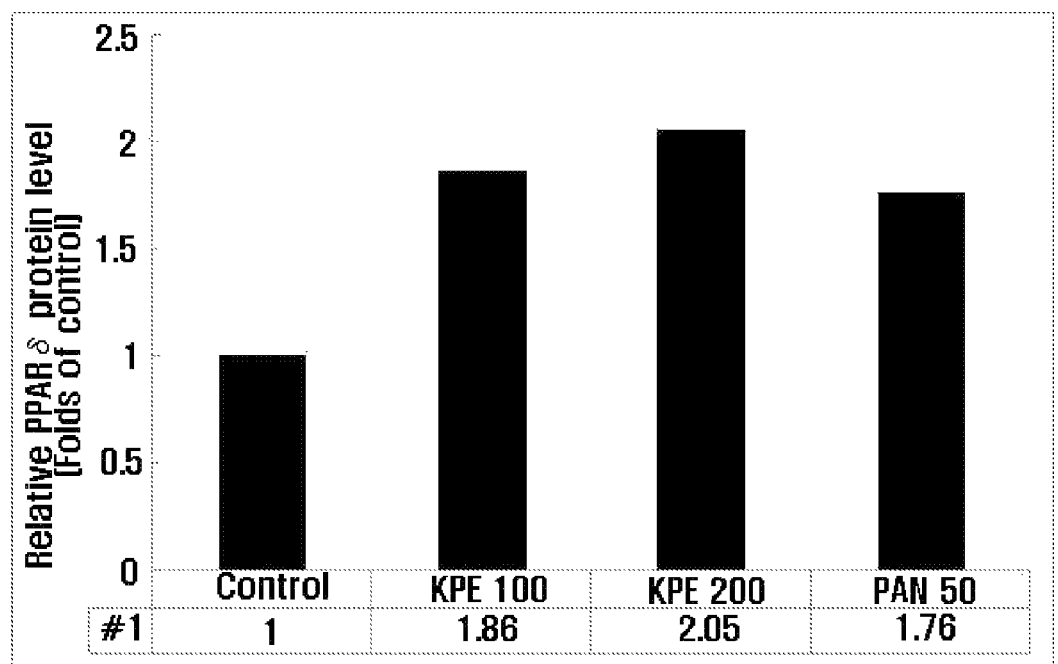
FIG. 1 shows the results of measuring the expression levels of PPAR-δ protein in a high-fat diet control group and a group administered with each of 100 mg/kg/day of an extract of *Boesenbergia pandurata* (KPE 100), 200 mg/kg/day of an extract of *Boesenbergia pandurata* (KPE 200) and panduratin A (PAN 50).

Hereinafter, the present invention will be described in detail with reference to examples. It is to be understood, however, these examples are for illustrative purposes only and are not intended to limit the scope of the present invention.

Example 1

Preparation of the Extract of *Boesenbergia pandurata* Containing Panduratin

Dried *Boesenbergia pandurata* was crushed in a mixer, and 100 g of the crushed *Boesenbergia pandurata* sample was extracted in 500 mL of ethanol with stirring at 50° C. for 30 minutes. The extracted sample was filtered twice through Whatman No. 2 filter paper, and the filtered extract was concentrated in a vacuum rotary evaporator to remove the solvent, after which it was freeze-dried to remove water, thereby obtaining an extract of *Boesenbergia pandurata*.

Example 2

Isolation and Determination of Structure of Panduratin A 2-1: Isolation of Panduratin A The concentrated extract of *Boesenbergia pandurata* obtained in Example 1 was mixed with ethyl acetate, and an ethyl acetate soluble component was extracted from the mixture and concentrated under reduced pressure to remove ethyl acetate. The concentrated component was loaded into a column packed with 615 cm silica gel and was fractionated using a solvent system consisting of hexane, chloroform and ethyl acetate mixed with each other at a ratio of 15:5:1.5 (v/v/v). The concentrated component was divided into a total of six fractions according to the order of fractionation, and each of the fractions was concentrated and dried. Among the six fractions, No. 3 fraction (fraction 3) was subjected to thin film chromatography (TLC, silica gel 60F254, Merck) using a developing solvent consisting of hexane, ethyl acetate and methanol mixed with each other at a ratio of 18:2:1 (v/v/v) to obtain a total of three fractions according to the order of fractionation, and the fractions were concentrated and dried. Among the three fractions, No. 2 fraction (fraction 32) was subjected to recycling HPLC, column (W252, 20.0 mm ID and 500 mm L) to obtain a total of two fractions according to the order of fractionation, and each of the fractions was concentrated and dried. Finally, among the two fractions, No. 2 fraction (fraction 322) was concentrated and dried, thereby isolating a single pure active substance.

2-2: Determination of Structure of Panduratin A

In order to determine the structure of the single active substance isolated in Example 2-1, the $^1$H-NMR spectrum and $^{13}$C-NMR spectrum of the single active substance were measured at 500 MHz and 125 MHz (solvent: $CDCl_3$), respectively. In order to measure $^1$H-$^1$H correlation and $^1$H-$^{13}$C correlation on the basis of the results of the obtained $^{13}$C-NMR spectrum and $^1$H-NMR spectrum, the $^1$H-$^1$H COSY spectrum and $^1$H-$^{13}$C HSQC spectrum of the active substance were measured, and the signal of each carbon was identified using a wavelength from carbon resonance.

In addition, for the mass spectrometry of the isolated single substance, the EI/MS was measured. In the EI/MS, [M$^+$H$^+$] was observed at m/z 407, and thus this compound was found to have a molecular weight of 406 and a molecular formula of $C_{26}H_{30}O_4$.

The results of the above $^1$H-NMR, $^{13}$C-NMR, $^1$H-$^1$H COSY, $^1$H-$^{13}$C HSQC and EI/MS were analyzed comparatively with a previous study report (Woo, W. S. et al., Phytochemistry, 26: 15421543, 1987). As a result, it was found that the single substance isolated in Example 2-1 was (2,6-dihydroxy-4-methoxyphenyl)[3-methyl-2-(3-methylbut-2-enyl)-5-phenylcyclohex-3-enyl]methanone which is a panduratin A compound represented by the following formula 1:

[Formula 1]

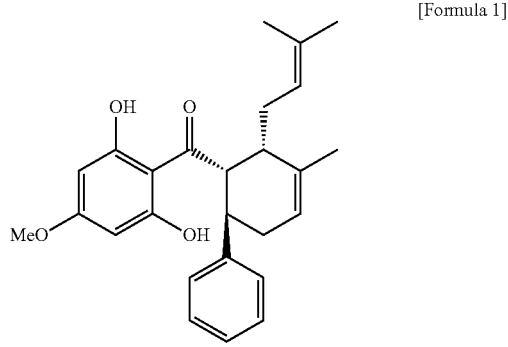 [SMILES: COc1cc(O)c(C(=O)[C@@H]2[C@H](CC=C(C)C)C(C)=CC[C@H]2c2ccccc2)c(O)c1]

Example 3

Effects of the Extract of *Boesenbergia pandurata* and Panduratin A on Expression of PPAR Protein 3-week-old C57BL/6 were acclimated for 1 week and fed with a high-fat diet (Product#D12492, Research Diet Inc., New Brunswick, N.J., USA) for 7 weeks to induce obesity. Then, the mice were randomly divided according to weight into a total of 3 groups, each consisting of 8 mice. Each of panduratin A and the extract of *Boesenbergia pandurata* was suspended in 0.25% carboxymethylcellulose, after which the mice of the test groups were administered with each of 50 mg/kg weight of panduratin A (PAN 50), 100 mg/kg weight of the extract of *Boesenbergia pandurata* (KPE 100) and 200 mg/kg weight of the *Boesenbergia pandurata* extract (KPE 200) once a day for 8 weeks at a predetermined time point. A control group was administered with a high-fat diet contained in the same amount of 0.25% carboxymethylcellulose as the intake of each test group. After administering the samples for 8 weeks, the mice were fasted and then the abdomen of each mouse was incised, after which the muscle tissue was extracted and stored at −70° C. until use. 100 mg of the muscles separated from each mouse of each group were homogenized in lysis buffer, and then analyzed by Western blotting using PPAR-δ antibody.

As a result, as can be seen in FIG. 1, the expression of PPAR-δ in the group administered with each of panduratin A and the extract of *Boesenbergia pandurata* increased compared to that in the control group. Because PPAR-δ acts as a transcription factor of type 1 skeletal muscle fiber, it can be predicted that an increase in the expression of PPAR-δ leads to an increase in the amount of type 1 skeletal muscle fibers. In addition, the expression of PPAR-δ in the group administered with KPE 200 was higher than that in the group administered with KPE 100, suggesting that the effect of the extract of *Boesenbergia pandurata* on the expression of PPAR-δ was concentration-dependent.

Example 4

Effects of *Boesenbergia pandurata* Extract and Panduratin a on Increase in Muscle Mass 3-week-old C57BL/6 were acclimated for 1 week and fed with a high-fat diet (Product#D12492, Research Diet Inc., New Brunswick, N.J., USA) for 7 weeks to induce obesity. Then, the mice were randomly divided according to weight into a total of 3 groups, each consisting of 8 mice. Each of panduratin A and the extract of *Boesenbergia pandurata* was suspended in 0.25% carboxymethylcellulose, after which the mice of the test groups were administered with each of 50 mg/kg weight of panduratin A (PAN 50), 100 mg/kg weight of the extract of *Boesenbergia pandurata* (KPE 100) and 200 mg/kg weight of the extract of *Boesenbergia pandurata* (KPE 200) once a day for 8 weeks at a predetermined time point. A control group was administered with a high-fat diet contained in the same amount of 0.25% carboxymethylcellulose as the intake of each test group. After administration of the samples for 8 weeks, the total muscle volume of each mouse and the muscle volume of each tissue were measured using micro-computed tomography.

Figure 2:
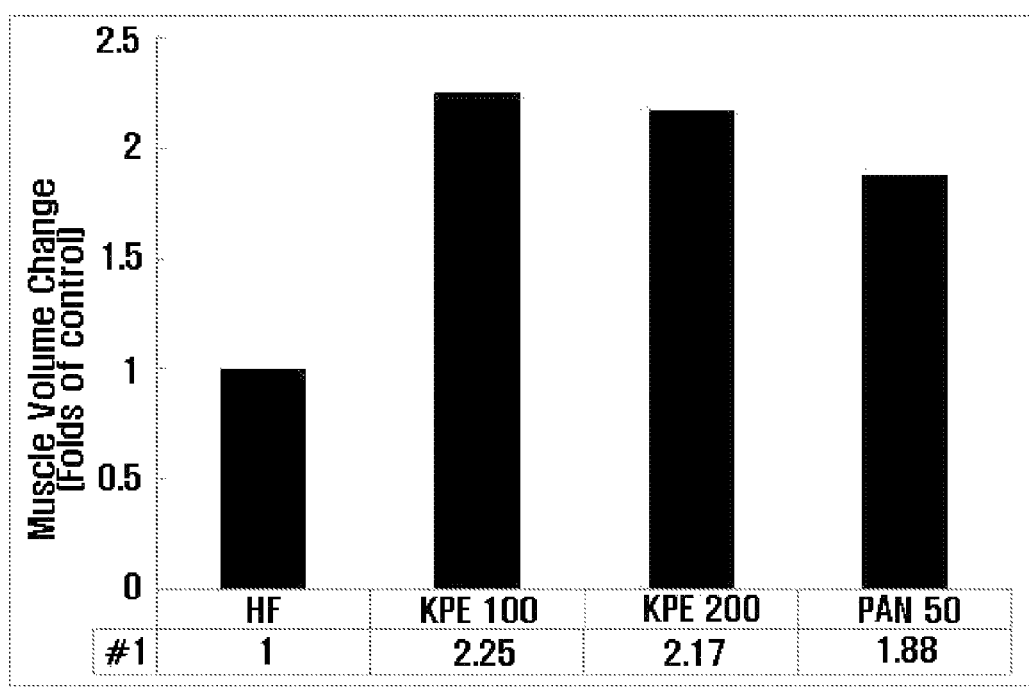
FIG. 2 shows the results of measuring increases in muscle volume of each of a high-fat diet control group and a group administered with each of 100 mg/kg/day of an extract of *Boesenbergia pandurata* (KPE 100), 200 mg/kg/day of an extract of *Boesenbergia pandurata* (KPE 200) and panduratin A (PAN 50).

As a result, as can be seen in FIG. 2, the volume of muscles in the group administered with each of panduratin A and the extract of *Boesenbergia pandurata* increased compared to that in the control group. The groups administered with the extract of *Boesenbergia pandurata* showed an at least 2-fold increase in muscle volume compared to the control group, and this increase is believed to be attributable to an increase in the expression of PPAR-δ in muscles. In addition, the group administered with panduratin A showed a 1.88-fold increase in muscle volume compared to the control group.

Example 5

Treadmill Test 3-week-old C57BL/6 were acclimated for 1 week and fed with a high-fat diet (Product#D12492, Research Diet Inc., New Brunswick, N.J., USA) for 7 weeks to induce obesity. Then, the mice were randomly divided according to weight into a total of 3 groups, each consisting of 8 mice. Each of panduratin A and the extract of *Boesenbergia pandurata* was suspended in 0.25% carboxymethylcellulose, after which the mice of the test groups were administered with each of 50 mg/kg weight of panduratin A (PAN 50), 100 mg/kg weight of the extract of *Boesenbergia pandurata* (KPE 100) and 200 mg/kg weight of the extract of *Boesenbergia pandurata* (KPE 200) once a day for 8 weeks at a predetermined time point. A control group was administered with a high-fat diet contained in the same amount of 0.25% carboxymethylcellulose as the intake of each test group. After administration of the samples for 8 weeks, the exercise capability of each mouse was measured using Exer-3R treadmill at a gradient of 10% at a speed of 11 m/min.

Figure 3:
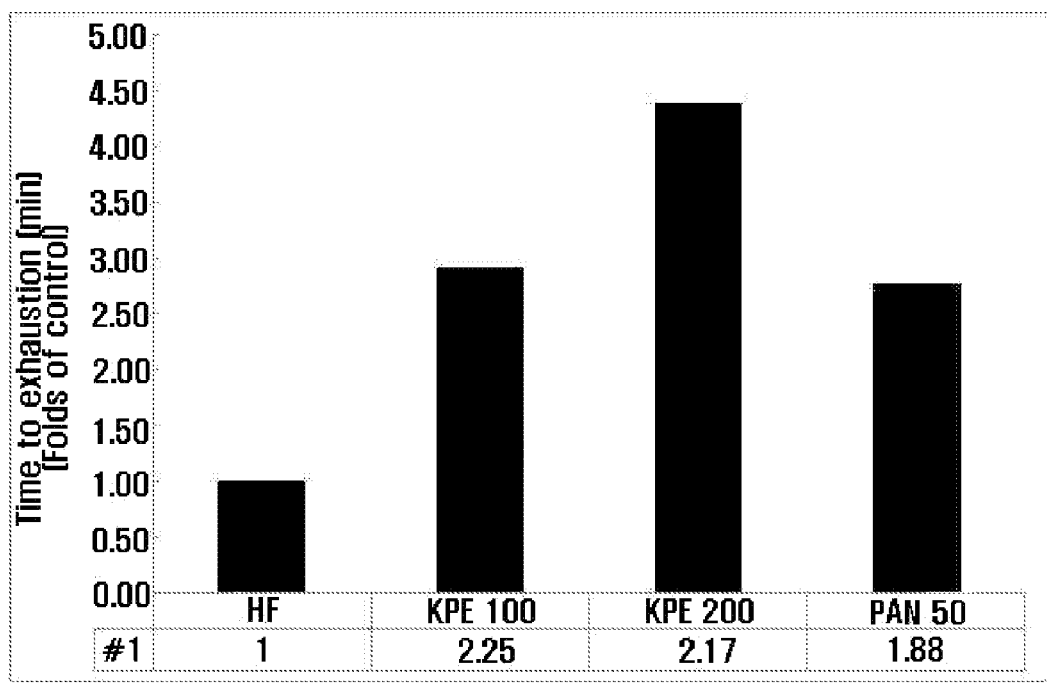
FIG. 3 shows the results of measuring the time to exhaustion of each of a high-fat diet control group and a group administered with each of 100 mg/kg/day of an extract of *Boesenbergia pandurata* (KPE 100), 200 mg/kg/day of an extract of *Boesenbergia pandurata* (KPE 200) and panduratin A (PAN 50) in order to measure the effect of improving mobility.

The time of movement induced by electrical stimulation was measured. As a result, as can be seen in FIG. 3, the mice of the group administered with 200 mg/kg weight of the extract of *Boesenbergia pandurata* (KPE 200) showed a 4.38-fold increase in mobility compared to the high-fat diet control group. Also, the group administered with 100 mg/kg weight of the extract of *Boesenbergia pandurata* (KPE 100) and the group administered with panduratin A (PAN 50) showed 2.92-fold and 2.77-fold increases in mobility, respectively, which were somewhat lower than that of KPE 200. Such results are similar to those of the test for the intramuscular expression of PPAR-δ and show that mobility increases in a manner dependent on the concentration of the extract of *Boesenbergia pandurata*.

INDUSTRIAL APPLICABILITY

As seen foregoing, the present invention provides a composition (or a method, use) for enhancing muscle mass growth, an anti-fatigue composition and a composition for enhancing exercise performance comprising a panduratin derivative or a salt thereof or an extract of *Boesenbergia pandurata*. A panduratin derivative or a salt thereof or an extract of *Boesenbergia pandurata* of the present invention may be used without side effect and has the effect of increasing the expression of PPAR-δ in muscles to increase muscle mass, promoting recovery from fatigue and increase mobility, thereby improving exercise performance.

The invention claimed is:
1. A method for enhancing muscle mass growth and increasing muscle strength in a human in need thereof comprising administering to said human in need thereof a therapeutically effective amount of an isolated compound selected from the group consisting of Formula 1, Formula 2, and Formula 3 to effectively enhance muscle mass growth and increase muscle strength in said human in need thereof

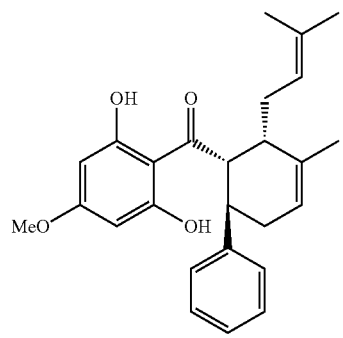

[Formula 1]

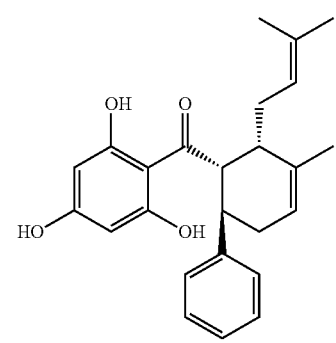

[Formula 2]

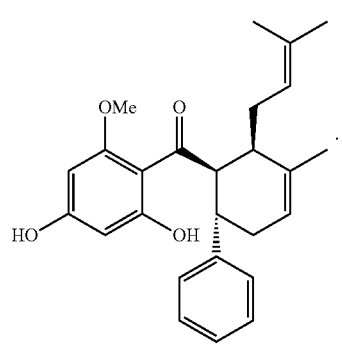

[Formula 3]

* * * * *